United States Patent
Al Taweel

(10) Patent No.: US 10,363,121 B1
(45) Date of Patent: Jul. 30, 2019

(54) KIT FOR MEASURING VERTICAL DIMENSION FOR DENTAL RESTORATION

(71) Applicant: KING SAUD UNIVERSITY, Riyadh (SA)

(72) Inventor: Sara Mohammad Al Taweel, Riyadh (SA)

(73) Assignee: King Saud University, Riyadh (SA)

( * ) Notice: Subject to any disclaimer, the term of this patent is extended or adjusted under 35 U.S.C. 154(b) by 3 days.

(21) Appl. No.: 15/878,365

(22) Filed: Jan. 23, 2018

(51) Int. Cl.
*A61C 19/04* (2006.01)
*A61K 6/10* (2006.01)

(52) U.S. Cl.
CPC .............. *A61C 19/04* (2013.01); *A61K 6/10* (2013.01)

(58) Field of Classification Search
CPC ............ A61C 19/04; A61C 19/05; A61K 6/10
USPC ...................................... 433/72–76
See application file for complete search history.

(56) References Cited

U.S. PATENT DOCUMENTS

| | | | |
|---|---|---|---|
| 3,153,282 A * | 10/1964 | Brewer ................ | A61C 19/05 433/214 |
| 3,381,377 A | 5/1968 | Grayson | |
| 3,686,754 A * | 8/1972 | Kondoloff ............ | A61C 9/00 433/223 |
| 3,695,333 A * | 10/1972 | Costa ................. | A61C 13/0003 164/35 |
| 3,763,565 A * | 10/1973 | Faust ................. | A61C 9/00 433/167 |
| 4,718,850 A | 1/1988 | Knebelman | |
| 8,899,983 B2 | 12/2014 | Kim | |
| 9,199,120 B2 | 12/2015 | Hutchinson | |
| 9,545,294 B2 | 1/2017 | Liebman | |
| 2007/0231774 A1 | 10/2007 | Massad | |
| 2008/0202530 A1* | 8/2008 | Sims ................. | A61C 7/36 128/845 |
| 2011/0125304 A1* | 5/2011 | Schneider ........... | A61C 13/0004 700/98 |

* cited by examiner

*Primary Examiner* — Matthew M Nelson
(74) *Attorney, Agent, or Firm* — Richard C. Litman

(57) ABSTRACT

The kit for measuring vertical dimension for dental impression provides a tool for measuring a difference between a dental patient's desired vertical dimension and the patient's vertical dimension prior to a dental restoration procedure. The kit includes a base, a plurality of measurement sheets, and dental impression wax. The base includes a planar member having first and second longitudinally opposed ends and opposed upper and lower surfaces. The upper surface has at least one longitudinally extending groove defined therein. First and second legs are secured to the first and second longitudinally opposed ends of the planar member and extend downward from the lower surface. Each measurement sheet has opposed upper and lower surfaces and at least one longitudinally extending rib formed on the lower surface and at least one longitudinally extending groove defined in the upper surface. Each of the plurality of measurement sheets has a known thickness.

3 Claims, 3 Drawing Sheets

KIT FOR MEASURING VERTICAL DIMENSION FOR DENTAL RESTORATION

BACKGROUND

1. Field

The disclosure of the present patent application relates to dental restoration, and particularly to a kit for measuring a difference between a dental patient's desired vertical dimension and the patient's vertical dimension prior to a dental restoration procedure.

2. Description of the Related Art

In dental restoration, casts of the maxillary (i.e., upper) and mandibular (i.e., lower) teeth of the patient are typically made, and the casts are then moved to an articulator. A dental articulator is a mechanical device to which the maxillary cast and the mandibular cast are fixed, reproducing recorded positions of the mandible in relation to the maxilla. An articulator assists in the fabrication of removable prosthodontic appliances (e.g., dentures), fixed prosthodontic restorations (e.g., crowns, bridges, inlays and onlays) and orthodontic appliances. With respect to the vertical dimension (i.e., the vertical distance between the patient's maxillary and mandibular teeth), the measured vertical dimension may not be the desired vertical dimension. This is particularly true for patients in whom one or more teeth have been ground down, typically due to bruxism, injury or disease. In such cases, the positions recorded by using the articulator will be representative of the patient's present shortened teeth, rather than the patient's teeth with the desired vertical dimension.

During dental restoration for patients with teeth that have been ground down, such as those described above, the dentist typically manually adjusts the articulator based on a visual estimate of the desired vertical dimension. In order to provide the patient with the highest level of care, and prevent having to repeat the dental restoration process multiple times, it would obviously be desirable to be able to accurately measure the difference between the patient's desired vertical dimension and the patient's vertical dimension prior to the dental restoration procedure (i.e., with the patient's original worn teeth) Thus, a kit for measuring vertical dimension for dental restoration solving the aforementioned problems are desired.

SUMMARY

The kit for measuring vertical dimension for dental restoration provides a tool for measuring a difference between a dental patient's desired vertical dimension and the patient's vertical dimension prior to a dental restoration procedure. The kit includes a base, a plurality of measurement sheets, and dental impression wax. The base includes a planar member having first and second longitudinally opposed ends and opposed upper and lower surfaces. The upper surface has at least one longitudinally extending groove formed therein. First and second legs extend from the first and second longitudinally opposed ends of the planar member and project downward from the lower surface. The first and second legs are spaced apart to define a gap therebetween.

Each measurement sheet has opposed upper and lower surfaces, at least one longitudinally extending rib formed on the lower surface thereof, and at least one longitudinally extending groove formed in the upper surface thereof. Each of the plurality of measurement sheets has an identical known thickness.

In use, the base is removably placed about at least one tooth of the patient such that the at least one tooth is positioned in the gap between the first and second legs. Preferably, a portion of the dental impression wax is sandwiched between the lower surface of the planar member and at least one coronal face of the at least one tooth. The lower surface of the planar member may be textured to grip the dental impression wax such that the base is stably held on the at least one tooth with the at least one coronal face being positioned adjacent the lower surface of the planar member, and the first and second legs being positioned about the side edges of the at least one tooth.

The at least one longitudinally extending rib of a first one of the plurality of measurement sheets is releasably received within the at least one longitudinally extending groove formed in the upper surface of the planar member, the measurement sheet defining an initial vertical dimension increment. Additional measurement sheets are stacked on the first one of the plurality of measurement sheets, with the at least one longitudinally extending rib of each of the additional ones of the plurality of measurement sheets being releasably received within the at least one longitudinally extending groove of an adjacent one of the plurality of measurement sheets, until the desired vertical dimension above the at least one coronal face is achieved.

Once the desired vertical dimension has been achieved, the base and the stacked measurement sheets are removed from the patient's mouth and the number of stacked measurement sheets is counted. Each measurement sheet has an identical thickness, which is known. Thus, the number of stacked measurement sheets is representative of the difference between the desired vertical dimension and the patient's vertical dimension prior to the dental restoration procedure (i.e., with the patient's original worn teeth).

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
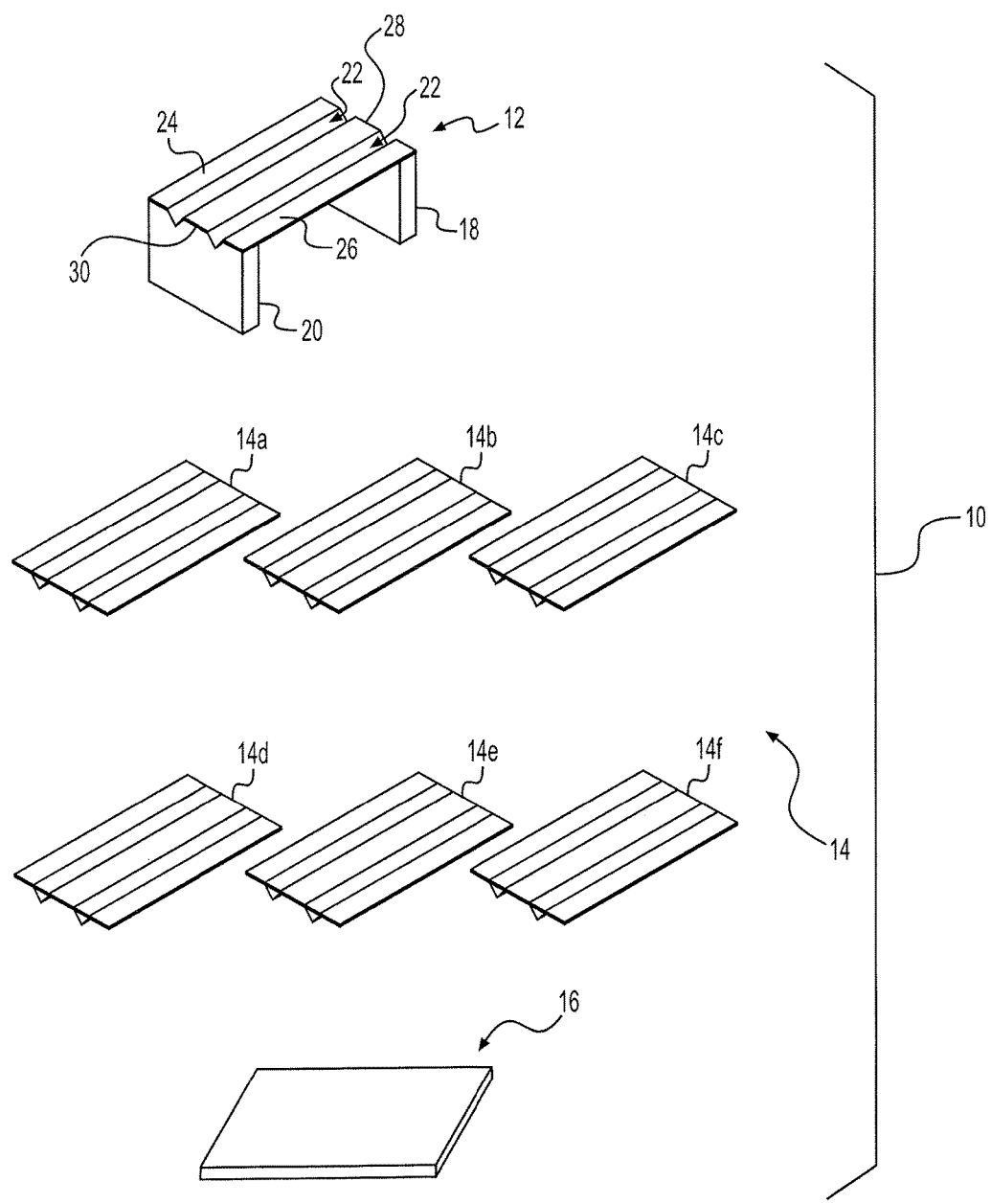
FIG. 1 is a perspective view of a kit for measuring vertical dimension for dental restoration.
Figure 2:
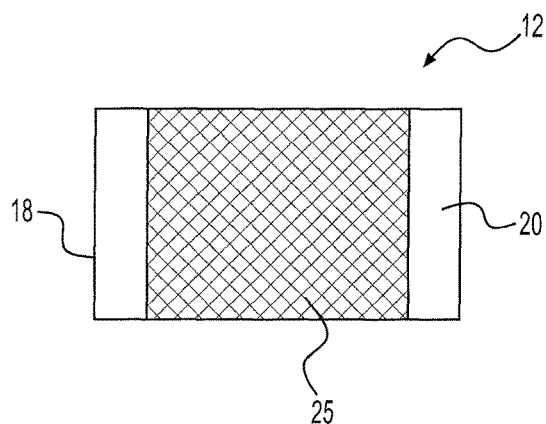
FIG. 2 is a bottom view of the base of the kit of FIG. 1.

Referring to FIG. 1, the kit 10 for measuring vertical dimension for dental restoration includes a base 12, a plurality of measurement sheets 14, and dental impression wax 16. As shown in FIGS. 1 and 2, the base 12 includes a planar member 26, having first and second longitudinally opposed ends 28, 30, respectively, and opposed upper and lower surfaces 24, 25, respectively. The upper surface 24 has at least one longitudinally extending groove 22 formed therein. Although FIG. 1 shows upper surface 24 having a pair of grooves 22 formed therein, it should be understood that the pair of grooves 22 are shown for exemplary purposes only, and that one or more grooves 22 may be formed in the upper surface 24. Additionally, first and second legs 18, 20 are respectively secured to the first and second longitudinally opposed ends 28, 30 of the planar member 26 and extend downward from the lower surface 25. As shown, the first and second legs 18, 20 are spaced apart to define a gap therebetween.

Figure 3A:
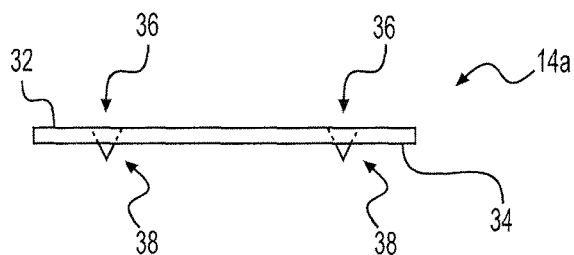
FIG. 3A is a side view of a measurement sheet of the kit of FIG. 1.
Figure 3B:
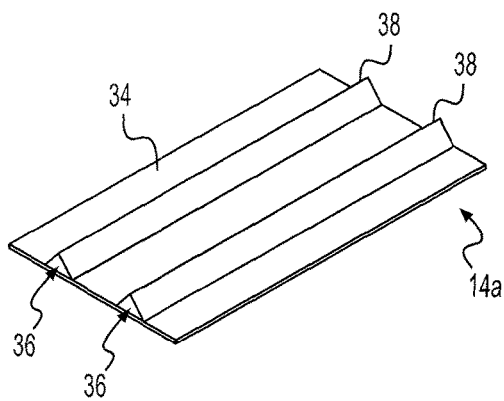
FIG. 3B is a bottom perspective view of the measurement sheet of FIG. 3A.

Although FIG. 1 shows six measurement sheets 14a, 14b, 14c, 14d, 14e and 14f, it should be understood that these six measurement sheets of the plurality of measurement sheets 14 are shown for purposes of illustration and simplification only, and that the plurality of measurement sheets 14 may contain any desired number of individual measurement sheets. Further, although FIGS. 3A and 3B show measurement sheet 14a alone, it should be understood that each individual measurement sheet of the plurality of measurement sheets 14 is identical. As shown in FIGS. 3A and 3B, measurement sheet 14a has opposed upper and lower surfaces 32, 34, respectively, with at least one longitudinally extending rib 38 formed on the lower surface 34 and at least one longitudinally extending groove 36 formed in the upper surface 32. Each of the plurality of measurement sheets 14 has an identical known thickness.

Although FIGS. 1, 3A and 3B show each of the measurement sheets 14 having a pair of grooves 36 formed in the upper surface 32 and a corresponding pair of ribs 38 projecting downward from the lower surface 34, it should be understood that the pair of grooves 36 and the pair of ribs 38 are shown for exemplary purposes only, and that one or more grooves 36 and one or more ribs 38 may be formed in each of the measurement sheets. The selected number of grooves 36 and number of ribs 38 are equal for each of the measurement sheets 14 (which, as noted above, are each identical with respect to one another), and are also equal to the number of grooves 22 formed in the upper surface 24 of the planar member 26 of the base 12. The ribs 38 are dimensioned and configured for alternately seating in the groove 22 defined in the upper surface 24 of the base 12 and the groove 36 defined in the upper surface 32 of the measurement sheets 14a-14f in order to interchangeably stack a variable number of the measurement sheets 14a-14f on the upper surface 24 of the base 12 to the height required for the dental restoration.

Figure 4A:
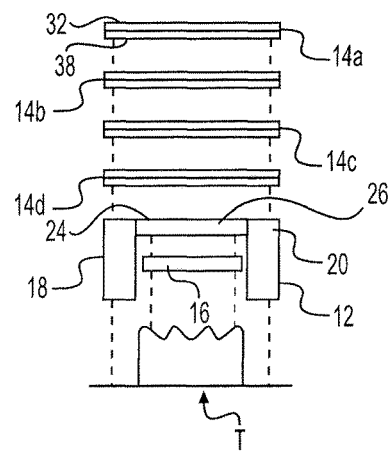
FIG. 4A is an exploded environmental front view of a kit for measuring vertical dimension for dental restoration, showing the order of components used for measuring the vertical dimension of a patient's teeth.
Figure 4B:
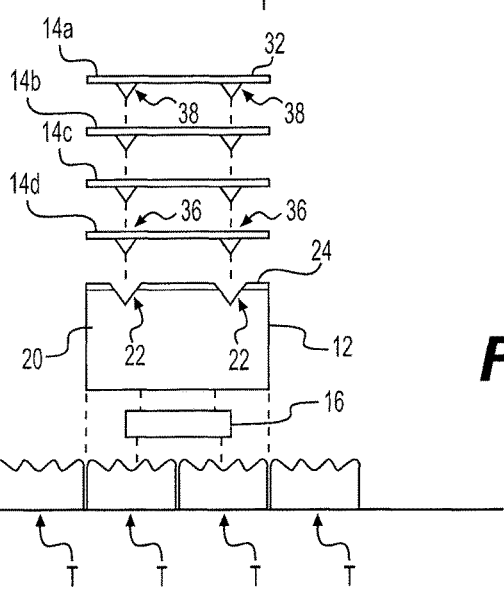
FIG. 4B is an exploded environmental side view of the kit of FIG. 4A.

In use, as illustrated in FIGS. 4A and 4B, the base 12 is removably placed about at least one tooth T of the patient, such that the at least one tooth T is positioned in the gap between the first and second legs 18, 20. Preferably, a portion of the dental impression wax 16 is sandwiched between the lower surface 25 of the planar member 26 and at least one coronal face of the at least one tooth T. The lower surface 25 of the planar member 26 may be textured, serrated, or knurled to grip the dental impression wax 16 such that the base 12 is stably held onto the at least one tooth T with the at least one coronal face being positioned adjacent the wax 16 beneath the lower surface 25 of the planar member 26, and the first and second legs 18, 20 being positioned about the side edges of the at least one tooth T. It should be understood that any suitable type of wax or other biocompatible and easily removable material may be used to temporarily secure the lower surface 25 to the at least one tooth T.

Figure 4C:
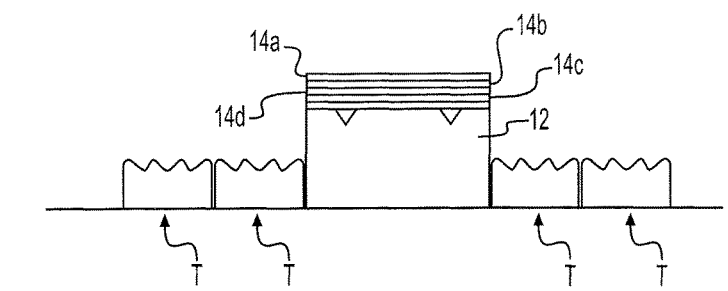
FIG. 4C is an environmental side view of the kit of FIGS. 4A-4B, shown in use for measuring the vertical dimension of a patient's teeth.

The at least one longitudinally extending rib 38 of a first one of the plurality of measurement sheets (measurement sheet 14d in the example of FIGS. 4A-4C) is releasably received within the at least one longitudinally extending groove 22 formed in the upper surface 24 of the planar member 26, defining an initial vertical dimension increment. If further increments of vertical dimension are to be added, additional ones of the plurality of measurement sheets (measurement sheets 14a, 14b and 14c in the example of FIGS. 4A-4C) are stacked on the first one of the plurality of measurement sheets 14d, with the at least one longitudinally extending rib 38 of each of the additional ones of the plurality of measurement sheets being releasably received within the at least one longitudinally extending groove 36 of an adjacent one of the plurality of measurement sheets, until the desired vertical dimension above the at least one coronal face is achieved. FIG. 4C represents the completed stacking of the desired number of measurement sheets 14 to achieve the desired additional vertical dimension for the at least one tooth T.

Once the desired vertical dimension has been achieved, the base 12 and the stacked ones of the plurality of measurement sheets (14a, 14b, 14c and 14d in the example of FIG. 4C) are removed from the patient's mouth and the number of stacked measurement sheets is counted (four measurement sheets in this example). Each measurement sheet has an identical thickness, which is known. Thus, the number of stacked measurement sheets plus the thickness of the planar member of the base is representative of the difference between the desired vertical dimension and the patient's vertical dimension prior to the dental restoration procedure (i.e., with the patient's original worn teeth).

It should be understood that the kit 10 may be provided with bases 12 and measurement sheets 14 manufactured in a variety of different sizes, thus providing kits which may be used, for example, with adult teeth, children's teeth, different types of teeth, etc. Each of the plurality of measurement sheets 14 preferably has a thickness that may be easily counted for the overall vertical dimension difference applied to the dental articulator during the dental restoration process. For example, each of the measurement sheets may have a thickness of 1 mm.

It is to be understood that the kit for measuring vertical dimension for dental restoration is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A kit for measuring vertical dimension for dental restoration, the kit consisting of:
   a base consisting of:
      a planar member having first and second longitudinally opposed ends, transversely opposed side edges and opposed upper and lower surfaces, the upper surface having a plurality of longitudinally extending parallel grooves defined therein; and
      first and second legs extending from the first and second longitudinally opposed ends of the planar member and projecting downward from the lower surface, the first and second legs defining a gap therebetween; and a plurality of measurement sheets, each of the measurement sheets consisting of opposed upper and lower surfaces and a plurality of longitudinally extending ribs projecting from the lower surface of the sheet and a plurality of longitudinally extending grooves defined in the upper surface of the sheet, each of the plurality of ribs projecting from the sheet being dimensioned and configured for alternately seating in the corresponding groove defined in the upper surface of the base and the upper surface of the measurement sheets in order to interchangeably stack a variable number of the measurement sheets on the upper surface of the base, each of the plurality of measurement sheets having an equal thickness and being dimensioned and configured to extend coextensively with the entire upper surface of the base from end to end and side edge to side edge, whereby the base is adapted for removable placement about at least one tooth of a patient in need of dental restoration such that the at least one tooth is positioned in the gap between the first and second legs, at least one coronal face of the at least one tooth being positioned below the lower surface of the planar member, so that the vertical dimension needed to compensate for worn teeth may be estimated by stacking the measurement sheets on the base to a height desired for the dental restoration.

2. A kit for measuring vertical dimension for dental restoration, the kit consisting of:
a base consisting of:
   a planar member having first and second longitudinally opposed ends, transversely opposed side edges and opposed upper and lower surfaces, the upper surface having a plurality of longitudinally extending parallel grooves defined therein; and
   first and second legs extending from the first and second longitudinally opposed ends of the planar member and projecting downward from the lower surface, the first and second legs defining a gap therebetween;
dental impression wax for attaching the base above a tooth; and
a plurality of measurement sheets, each of the measurement sheets consisting of opposed upper and lower surfaces and a plurality of longitudinally extending ribs projecting from the lower surface of the sheet and a plurality of longitudinally extending grooves defined in the upper surface of the sheet, each of the plurality of ribs projecting from the sheet being dimensioned and configured for alternately seating in the corresponding groove defined in the upper surface of the base and the upper surface of the measurement sheets in order to interchangeably stack a variable number of the measurement sheets on the upper surface of the base, each of the plurality of measurement sheets having an equal thickness and being dimensioned and configured to extend coextensively with the entire upper surface of the base from end to end and side edge to side edge, whereby the base is adapted for removable placement about at least one tooth of a patient in need of dental restoration such that the at least one tooth is positioned in the gap between the first and second legs, at least one coronal face of the at least one tooth being positioned below the lower surface of the planar member, so that the vertical dimension needed to compensate for worn teeth may be estimated by stacking the measurement sheets on the base to a height desired for the dental restoration.

3. The kit for measuring vertical dimension as recited in claim 2, wherein the lower surface of the planar member is textured for engaging at least a portion of the dental impression wax.

* * * * *